US008197258B2

(12) United States Patent
Delahunt et al.

(10) Patent No.: US 8,197,258 B2
(45) Date of Patent: Jun. 12, 2012

(54) COGNITIVE TRAINING USING FACE-NAME ASSOCIATIONS

(75) Inventors: Peter B. Delahunt, San Mateo, CA (US); Joseph L. Hardy, Richmond, CA (US); Henry W. Mahncke, San Francisco, CA (US); Shruti Gangadhar, San Francisco, CA (US)

(73) Assignee: Posit Science Corporation, San Francisco, CA (US)

( * ) Notice: Subject to any disclaimer, the term of this patent is extended or adjusted under 35 U.S.C. 154(b) by 1529 days.

(21) Appl. No.: 11/611,252

(22) Filed: Dec. 15, 2006

(65) Prior Publication Data

US 2007/0218441 A1 Sep. 20, 2007

Related U.S. Application Data

(60) Provisional application No. 60/750,509, filed on Dec. 15, 2005, provisional application No. 60/762,434, filed on Jan. 26, 2006.

(51) Int. Cl.
*G09B 19/00* (2006.01)
(52) U.S. Cl. ........................................ 434/236; 434/322
(58) Field of Classification Search .................. 434/236, 434/322–365; 351/203, 237, 239
See application file for complete search history.

(56) References Cited

U.S. PATENT DOCUMENTS

| | | | |
|---|---|---|---|
| 4,971,434 A | 11/1990 | Ball | |
| 5,801,810 A | 9/1998 | Roenker | |
| 6,328,569 B1 | 12/2001 | Jenkins et al. | |
| 6,334,777 B1 | 1/2002 | Jenkins et al. | |
| 6,364,486 B1 | 4/2002 | Ball et al. | |
| 6,413,098 B1 | 7/2002 | Tallal et al. | |
| 6,464,356 B1 | 10/2002 | Sabel et al. | |
| 6,585,519 B1 * | 7/2003 | Jenkins et al. | 434/236 |
| 6,599,129 B2 | 7/2003 | Jenkins et al. | |
| 6,626,676 B2 | 9/2003 | Freer | |

(Continued)

FOREIGN PATENT DOCUMENTS

DE 69529054 8/2003

(Continued)

OTHER PUBLICATIONS

Campanella, S. et al. ; Association of the Distinct Visual Representations of Faces and Names: A PET Activation Study; NeuroImage 14, 873-882 (2001_.*

(Continued)

*Primary Examiner* — Timothy A Musselman
(74) *Attorney, Agent, or Firm* — James W. Huffman

(57) ABSTRACT

Computer-implemented method for enhancing the cognitive ability of a participant using face-name associations. A plurality of facial images of people are provided for visual presentation to the participant, each person having a name. A learning phase is performed, including concurrently presenting a first facial image of a person from the plurality of facial images, and the name of the person. A testing phase is then performed, including: presenting a second facial image of the person from the plurality of facial images, displaying a plurality of names, including the name of the person and one or more distracter names, requiring the participant to select the name of the person from the plurality of names, and determining whether the participant selected the name correctly. The learning phase and the testing phase are repeated one or more times in an iterative manner to improve the participant's cognition, e.g., face-name association skills.

31 Claims, 7 Drawing Sheets

U.S. PATENT DOCUMENTS

| | | | |
|---|---|---|---|
| 7,367,675 | B2 | 5/2008 | Maddalena et al. |
| 2003/0201982 | A1 | 10/2003 | Iesaka |
| 2005/0175972 | A1 | 8/2005 | Goldman et al. |
| 2005/0213033 | A1 | 9/2005 | Sabel |
| 2006/0161218 | A1 | 7/2006 | Danilov |
| 2006/0234199 | A1 | 10/2006 | Walker et al. |
| 2007/0166675 | A1 | 7/2007 | Atkins et al. |
| 2007/0166676 | A1 | 7/2007 | Bird et al. |
| 2007/0218439 | A1 | 9/2007 | Delahunt et al. |
| 2007/0218440 | A1 | 9/2007 | Delahunt et al. |
| 2007/0293732 | A1 | 12/2007 | Delahunt et al. |
| 2008/0084427 | A1 | 4/2008 | Delahunt et al. |

FOREIGN PATENT DOCUMENTS

| | | |
|---|---|---|
| EP | 00502984 | 12/1992 |
| EP | 1069855 | 8/2001 |
| WO | WO9952419 | 10/1999 |
| WO | WO03065964 | 8/2003 |

OTHER PUBLICATIONS

Schweinberger, Stefan R. et al.; Human Brain Potential Correlates of Repetitios Priming in Face and Name Recognition; Department of Psychology, University of Glasgow; Neuropsychologia 40 (2002) 2057-2073.*

Baudouin.pdf - Baudouin, Jean-Yves—Selective Attention to Facial Emotion and Identity in Schizophrenia—Neuropsychologia 40 (2002) pp. 503-511.*

Herlholz.pdf—Herlholz, Karl—Learning Face-Name associations and the effect of Age and Performance: A PET Activation Study—Neuropsychologia 39 (2001) pp. 643-650.*

Wallace.pdf—Wallace, Marie A.—Savings in Relearning Face-Name Associations as evidence for covert recognition in prosopagnosia 0—Carnagie Mellon University Department of Psychology, Pittsburgh, PA 15213—Jan. 1992.*

Sekuler et al. "Visual localization: age and practice." Optical Society of America. vol. 3, No. 6. Jun. 1986. pp. 864-867.

Ball et al. "Effects of Cognitive Training Interventions With Older Adults: A Randomized Controlled Trial." American Medical Association, Nov. 13, 2002, vol. 288, No. 18, pp. 2271-2281.

Su et al. "De-Emphasis of Distracting Image Regions Using Texture Power Maps." Computer Science and Artificial Intelligence Laboratory Technical Report. Apr. 12, 2005. Pages 1-12. Web Sep. 21, 2009. http://dspace.mit.edu/handle/1721.1/30537.

Phipps et al. "Fast Psychophysical Procedures for Clinical Testing." Clinical and Experimental Optometry 84.5 pp. 264-269. QUP ePrints. May 4, 2007. Web Sep. 21, 2009, http://eprints.qut.edu.au/7481/.

Pylyshyn, Zenon W. "Visual Indexes, Preconceptual Objects, and Situated Vision." Cognition 80 (2001) 127-158 Rutgers Center for Cognitive Sciences, Rutgers University, Psychology Building, New Wing, Busch Campus, New Brunswick, NJ 08903.

* cited by examiner

COGNITIVE TRAINING USING FACE-NAME ASSOCIATIONS

CROSS REFERENCE TO RELATED APPLICATION(S)

This application claims the benefit of the following U.S. Provisional Patent Applications, which are incorporated herein in their entirety for all purposes:

| Docket No. | Serial No. | Filing Date: | Title: |
|---|---|---|---|
| PS.0119 | 60/750509 | Dec. 15, 2005 | HAWKEYE ASSESSMENTS SPECIFICATION |
| PS.0121 | 60/762434 | Jan. 26, 2006 | COMPUTER BASED FACE-NAME ASSOCIATION TRAINING PROGRAM |

The following applications are related to the present application:

| | | | |
|---|---|---|---|
| PS.0217 | ******* | ******* | COGNITIVE TRAINING USING VISUAL SWEEPS |
| PS.0218 | ******* | ******* | COGNITIVE TRAINING USING VISUAL SEARCHES |
| PS.0219 | ******* | ******* | COGNITIVE TRAINING USING MULTIPLE OBJECT TRACKING |
| PS.0225 | ******* | ******* | COGNITIVE TRAINING USING EYE MOVEMENT |
| PS.0229 | ******* | ******* | COGNITIVE TRAINING USING VISUAL STIMULI |

FIELD OF THE INVENTION

This invention relates in general to the use of brain health programs utilizing brain plasticity to enhance human performance and correct neurological disorders, and more specifically, to a method for improving cognition, e.g., the ability of the visual nervous system to make face-name associations.

BACKGROUND OF THE INVENTION

Almost every individual has a measurable deterioration of cognitive abilities as he or she ages. The experience of this decline may begin with occasional lapses in memory in one's thirties, such as increasing difficulty in remembering names and faces, and often progresses to more frequent lapses as one ages in which there is passing difficulty recalling the names of objects, or remembering a sequence of instructions to follow directions from one place to another. Typically, such decline accelerates in one's fifties and over subsequent decades, such that these lapses become noticeably more frequent. This is commonly dismissed as simply "a senior moment" or "getting older." In reality, this decline is to be expected and is predictable. It is often clinically referred to as "age-related cognitive decline," or "age-associated memory impairment." While often viewed (especially against more serious illnesses) as benign, such predictable age-related cognitive decline can severely alter quality of life by making daily tasks (e.g., driving a car, remembering the names of old friends) difficult.

An important part of navigating everyday life is being able to recognize a familiar face and accurately associate it with a proper name. This ability is fundamental to personal, social, and professional life experiences. It is important to be able to correctly remember face-name associations in many environments encountered regularly, such as work, school, residential communities, and recreational activities that have a social component.

On the most basic level, this task requires the individual to first identify a face, to recall the appropriate name, and then finally be able to successfully associate or bind the two together. There is general agreement in literature on cognitive aging that episodic, recognition memory functioning declines with age. The degraded representational fidelity of the visual system in older adults causes an additional difficulty in the ability of older adults to store and use information in working memory. Anecdotal evidence indicates that a major complaint of older adults is their inability to recall the appropriate name of a familiar face they have seen in the past. What is less clear, however, is whether the inability to remember names of people is due to the reduced representational fidelity of the features (i.e., faces) of the person and the name per se, or whether there is a selective deficit for encoding and storing the face-name association. The associative deficit hypothesis (ADH) states that the loss in memory for people's names is due primarily to the inability to encode and store the face-name association. Results from ADH studies indicate that older and younger adults with similar performances on a face recognition task and a proper name recognition task differed significantly in their performance on a name-face associative recognition task. While there is generally a loss in representational fidelity for visual and verbal information in normal aging, results from ADH studies and related work suggests that there is an additional and selective deficit for face-name association related to age.

There have been efforts made to alleviate this problem. For example, online employee directories have been created to allow employees to search for people by last name, department and other factors to help get familiar with other employees. Mnemonic methods have also been suggested as a learning strategy that can assist in name/face association. Although these strategies are useful to some extent, they are limited because they do not employ strategies based on current knowledge of brain plasticity and methods for optimizing learning through attention, reward and novelty.

In many older adults, age-related cognitive decline leads to a more severe condition now known as Mild Cognitive Impairment (MCI), in which sufferers show specific sharp declines in cognitive function relative to their historical lifetime abilities while not meeting the formal clinical criteria for dementia. MCI is now recognized to be a likely prodromal condition to Alzheimer's Disease (AD) which represents the final collapse of cognitive abilities in an older adult. The development of novel therapies to prevent the onset of this devastating neurological disorder is a key goal for modern medical science.

The majority of the experimental efforts directed toward developing new strategies for ameliorating the cognitive and memory impacts of aging have focused on blocking and possibly reversing the pathological processes associated with the physical deterioration of the brain. However, the positive benefits provided by available therapeutic approaches (most notably, the cholinesterase inhibitors) have been modest to date in AD, and are not approved for earlier stages of memory and cognitive loss such as age-related cognitive decline and MCI.

Cognitive training is another potentially potent therapeutic approach to the problems of age-related cognitive decline, MCI, and AD. This approach typically employs computer- or clinician-guided training to teach subjects cognitive strategies to mitigate their memory loss. Although moderate gains in memory and cognitive abilities have been recorded with cognitive training, the general applicability of this approach has been significantly limited by two factors: 1) Lack of Generalization; and 2) Lack of enduring effect.

Lack of Generalization: Training benefits typically do not generalize beyond the trained skills to other types of cognitive tasks or to other "real-world" behavioral abilities. As a result, effecting significant changes in overall cognitive status would require exhaustive training of all relevant abilities, which is typically infeasible given time constraints on training.

Lack of Enduring Effect: Training benefits generally do not endure for significant periods of time following the end of training. As a result, cognitive training has appeared infeasible given the time available for training sessions, particularly from people who suffer only early cognitive impairments and may still be quite busy with daily activities.

As a result of overall moderate efficacy, lack of generalization, and lack of enduring effect, no cognitive training strategies are broadly applied to the problems of age-related cognitive decline, and to date they have had negligible commercial impacts. The applicants believe that a significantly innovative type of training can be developed that will surmount these challenges and lead to fundamental improvements in the treatment of age-related cognitive decline. This innovation is based on a deep understanding of the science of "brain plasticity" that has emerged from basic research in neuroscience over the past twenty years, which only now through the application of computer technology can be brought out of the laboratory and into the everyday therapeutic treatment.

Thus, improved systems and methods for improving the ability of the visual nervous system of a participant to associate faces and names are desired.

SUMMARY

Various embodiments of a system and method for improving a participant's cognition, e.g., renormalizing and improving the ability of the visual nervous system of a participant to associate faces with names, are presented. In preferred embodiments, the method may be performed in the context of a visual stimulus exercise, e.g., a face-name association exercise, possibly in combination with one or more other visual stimulus exercises.

A plurality of facial images of people may be provided, where each person has a name. The plurality of facial images may each be available for visual presentation to the participant. The plurality of facial images provided may depend on the context in which the exercise is performed. For example, in some embodiments, the exercise may be directed to improving name-face association of a participant with respect to people that are (or should be) familiar to the participant. As one example, the participant may be a resident of a facility, such as a nursing home, where the plurality of facial images may include those of co-residents and/or staff of the nursing home. As another example, the participant may be an employee of a company or institution, and the plurality of facial images may include those of the employees of the company or institution. Of course, these are but two examples of contexts with familiar faces, and any other such contexts are also contemplated, e.g., school, communities, etc. In these (familiar) contexts, in addition to improving cognition, e.g., improving face-name association skills in the participant, the exercise may further serve to familiarize the participant with the people with whom the participant interacts in the facility, company, or institution, thereby providing immediate and direct practical benefits, as well as improving the cognition of the participant.

In other embodiments, the plurality of facial images may not be familiar to the participant. For example, a large number (e.g., 300) of pictures of different faces (e.g., male and female between 18 and 90 years of age) may be used that include various different expressions, facial orientations, etc. In one embodiment, the pictures may be selected from a face database. In these (unfamiliar) contexts, the exercise may improve the cognitive skills of the participant (including, for example, memory skills), as well as improving the participant's particular skills of face-name association, which is of general benefit in social domains.

Note that in both kinds of context (familiar and unfamiliar faces), stimuli, i.e., facial images, with unusual features (e.g., hats) are preferably not used. The images may be standardized with respect to frame, size, luminosity and contrast. In higher stages of the exercise, morphing may be used to create ever-increasing difficulty in making face identifications.

A learning phase of the method or exercise may be performed, elements of which are described below. In the learning phase, the participant is given a chance to learn a face/name association, and then, in a subsequent testing phase, described below, the participant is tested with respect to this association, and possibly others. In one embodiment, this learning and testing with respect to a face/name pair may compose a trial in the exercise, although in other embodiments, a trial may comprise such learning and testing with respect to all faces and names in a trial group (e.g., five faces/names). The learning phase is now described. A first facial image of a person from the plurality of facial images may be presented. For example, the first facial image may be displayed in a display area of a graphical user interface (GUI).

The name of the person may be presented concurrently with the presenting of the first facial image. In other words, a first facial image of a person and the name of the person may be presented to the participant at the same time. Note that the name may be presented graphically and/or audibly (verbally). In other words, presenting the name may include textually presenting the name and/or auditorily presenting the name. Moreover, auditorily presenting the name may include a synchronous-onset presentation of the name with said presenting the facial image. In other words, the name may be played when the facial image is first displayed.

In some embodiments, presenting the first facial image may include flashing the facial image at a specified rate, e.g., between 1 and 4 Hz, although any other rate may be used as desired. Similarly, presenting the name of the person may include repeating the name at a specified rate (graphically and/or audibly), preferably the same rate at which the facial image is flashed. In one embodiment, the name may be presented graphically and verbally, where the graphical name is static, and the verbal presentation of the name is repeated with the facial image.

In preferred embodiments, the participant may perform the exercise described herein via a graphical user interface (GUI). The GUI preferably includes a visual field in which may be displayed a facial image of a person, e.g., the first facial image described above. As also described above, the GUI may also display the name of the person. As noted above, in some embodiments, the name may also (or instead) be verbally or audibly presented. Moreover, as also noted above, the face and verbal name may be repeated at a specified rate, e.g., for a specified time. The GUI may further include one or more of: a score indicator, an indicator of how many correct associations the participant has made, and indicator of how many incorrect association the participant has made, and a bonus meter that indicates how close the participant is to getting bonus points in each trial group. Of course, this GUI is meant to be exemplary only, and is not intended to limit the GUI to any particular form, functionality, or appearance.

In various embodiments, and over the course of the exercise, the presenting may be performed under a variety of specified conditions that may make performing the task more or less difficult. For example, the presentation time for the facial image and the name may be shortened to increase the difficulty of the task, or lengthened to make the task easier. Other conditions may also be used, such as, for example, the orientation or expression of the facial images, as will be described below in detail.

After the learning phase, a testing phase of the exercise may be performed, elements of which are described below. In the testing phase, the participant is tested with respect to the face/name presented in the learning phase, and may also be tested on previously presented face/name pairs, as will be discussed below. The testing phase is now described.

A second facial image of the person from the plurality of facial images may be presented. In some embodiments, the second facial image is the same image as the first facial image. However, in other embodiments, the second facial image and the first facial image may differ. For example, the first and second facial images of the person may differ in view and/or expression, where the view of a facial image refers to the orientation of the face, e.g., front view, profile, and so forth. In some embodiments, one or more of the first and second facial images may be morphed, i.e., stretched, compressed, or otherwise distorted, to increase the difficulty of the task.

A plurality of names, including the name of the person and one or more distracter names, may then be presented. These distracter names may include names of previously presented facial images and/or names not associated with any facial images. In preferred embodiments, the number of names presented may vary from trial to trial.

The participant may then be required to select the name of the person from the plurality of names. For example, input from the participant selecting the name may be received, and the selection made by the participant may be recorded. In one embodiment, the name may be selected by the participant placing a cursor over the name to be selected and clicking a mouse, although other selection means may be used as desired, e.g., using arrow keys to navigate through the list, and pressing the enter key, using a menu, etc. A determination may be made as to whether the participant selected the name correctly. The correctness or incorrectness of the selection is preferably recorded. In some embodiments, an indication of the correctness or incorrectness of the selection may be provided, e.g., graphically and/or audibly. It should be noted, however, that any other kind of indication may be used as desired, e.g., a reward animation, etc.

In one embodiment, points may be awarded based on the correctness of the selection, which may be reflected by the score indicator of the GUI. Similarly, in some embodiments, based on the correctness/incorrectness of the selection, the indicator of how many correct associations the participant has made or the indicator of how many incorrect associations the participant has made may be updated accordingly.

Finally, the above learning phase and testing phase may be performed one or more times in an iterative manner to improve the participant's cognition, e.g., face-name association skills.

In other words, a plurality of trials may be performed in the exercise as described above. For example, the repetitions may be performed over a plurality of sessions, e.g., over days, weeks, or even months, e.g., for a specified number of times per day, and for a specified number of days. In some embodiments, at the end of each session, the participant's score for the session may be shown and may be compared to the best prior performance for that participant.

Such repeating preferably includes performing a plurality of trials under each of a plurality of conditions, where each condition specifies one or more attributes of the plurality of images or their presentation. Thus, groups of stimuli, referred to as trial groups, may contain or embody particular conditions affecting the difficulty of the face-name association task. A typical trial group may include 5 faces/names, although other numbers may be used as desired. Thus, the plurality of facial images may include a plurality of groups of facial images, where the repeating may include: for each group, performing the learning phase and the testing phase for each facial image in the group.

For example, the plurality of facial images may include one or more stimulus categories, each stimulus category specifying a relationship between the first and second facial images in the stimulus category. In some embodiments, the one or more stimulus categories include one or more of: a single view category, where the first and second facial images have the same view, a multiple view category, where the first and second facial images have different views, and a multiple expression category, where the first and second facial images have different expressions. Thus, even though each facial image pair (i.e., the first and second facial images of the learning and testing phases) illustrates the same person, the images may (or may not) differ from each other. Thus, the repeating may include progressing through groups of facial images in each of the one or more stimulus categories.

In some embodiments, each category may have a respective plurality of subcategories further specifying the relationship between first and second facial images in the category. For example, the subcategories may include two or more of: an age and gender independent subcategory, where the person of the first and second facial images is unconstrained with respect to age and gender, a gender specific subcategory, where the person of the first and second facial images is constrained with respect to gender, and an age specific subcategory, where the person of the first and second facial images is constrained with respect to age. In these embodiments, progressing through groups of facial images in each of the one or more stimulus categories may include: for each stimulus category, progressing through groups of facial images in each subcategory of the stimulus category.

The participant may progress through a plurality of trial groups of the exercise based on the participant's success rate at each trial group, where each trial group may be associated with respective subsets of the conditions (e.g., one condition per trial group). Thus, for example, initial trial groups may include trials performed under the easiest conditions, and successive, more difficult, trial groups may include trials performed under more difficult conditions. An example of an easier trial group is one in which the names/faces in the group are all of the same gender, and in which the first and second facial images (of the learning phase and the testing phase, respectively) are the same. An example of a more difficult trial group is one in which the trial group includes faces/names of both genders, and where the first and second facial images differ in orientation (e.g., front view vs. profile) and facial expression (solemn vs. smiling). The trial groups may continue until the participant has mastered all the faces and names in all categories.

In some embodiments, the conditions of the stimuli (i.e., faces/names) used may depend upon the context of the exercise. For example, in some embodiments using familiar faces/names, the facial images may have various orientations and expressions (expressing various emotions, e.g., neutral/happy/sad/annoyed, etc.), mixed genders within a trial group, and so forth, whereas in some embodiments using unfamiliar faces/names, the facial images may all have the same orientation (e.g., front view) and expression (e.g., neutral), gender specific trial groups, etc. However, it should be noted that any conditions may be used as desired in both the familiar and unfamiliar contexts.

In some embodiments, the progression through each trial group may be progressive, where, for each face/name pair from the trial group presented to the participant, the participant is tested on that face/name pair, plus all face/name pairs previously presented from the trial group. Moreover, in some embodiments, one or more, e.g., two, additional face/name pairs from a previous trial group may also be included in the testing. The following describes an exemplary embodiment of such a progression.

In some embodiments, performing the testing phase for each facial image in the group may include: for each facial image in the group, referred to as the first group, and for each facial image in a second group including the facial image (or another facial image of the same person), previously presented facial images from the first group, and zero or more previously presented facial images from a previous group, a) presenting a randomly selected facial image of a person from the second group, b) displaying a second plurality of names, including the name for each facial image in the second group, and one or more distracter names, c) requiring the participant to select the name of the person for the randomly selected facial image from the plurality of names; and d) determining whether the participant correctly selected the name of the person for the randomly selected facial image.

In other words, after each face/name from the trial group, i.e., the first group, is presented in the learning phase, the participant is tested on all the faces/names in a second group, comprising the most recent face/name, all previously presented faces/names from the first (trial) group, plus one or more distracter names, plus zero or more faces/names from the previous trial group. Thus, each time a new face/name from the trial group is presented in the learning phase, the list of selectable names presented in the testing phase may increase by one. Said another way, as the participant progresses through the trial group, the number of names/faces tested on increases, as all previous faces/names are included in the testing. In various embodiments, the number of additional faces/names from the previous trial group used in the testing phase may be zero, one, two, or any other number, as desired. It should be noted that in various embodiments, the distracter name may be constant for a trial group, or may change, e.g., in response to the participant's selection(s), or even per selection task.

Moreover, in some embodiments, the repeating may further include: if the participant incorrectly selected the name of the person for the randomly selected facial image, performing the learning phase again for the randomly selected facial image, and performing a)-d) for each facial image in the second group. In other words, each time the participant selects a wrong name, the learning phase for the current face/name may be performed, then the above progressive learning phase. This repetition may serve to reinforce previously "learned" face/name pairs, and to accelerate the improvement of the participant's face/name association skills. Note also that as the participant makes correct associations, the task gets progressively harder as the participant has to remember all face-name pairs learned to that point (for that trial group).

As noted above, participants may move through all subcategories within a category before moving to the next category. Within each subcategory, participants move through trial groups or stages (i.e., with increasing numbers of response buttons) and then advance through categories or levels (age and gender specific) based on performance. Note that progression in the exercise is designed to allow participants with poor face-name association ability to advance through tasks without getting stuck by retraining them on the face-name pairs for which wrong associations are made.

In some embodiments, the initial trial group may be handled differently from subsequent trial groups. For example, no additional faces/names from previous trial groups may be included, since there are no previous trials groups initially. Thus, for example, with respect to the initial trial group, the possible selections for the first face/name association are limited to two names—the name of the person whose face is displayed, and one distracter name. In contrast, with respect to a subsequent (non-initial) trial group, at the start of the learning phase of the trial group the user is trained on a new face. However, during the test phase, unlike the first trial group, the user is tested on the new face and two randomly chosen faces from the previous trial group. As a result, beginning from the second trial group, all consecutive trials may end with being tested on seven face-name pairs (plus one distracter name).

In some embodiments, one or more assessments of the participant's face/name association skills may be made, e.g., before, during, and/or after the exercise. The stimuli (i.e., faces/names) used in the assessment may depend upon the context of the exercise. For example, in embodiments using familiar faces/names, the participant's knowledge (i.e., ability to associate) of all faces may be tested at the beginning and end of the exercise. In embodiments using unfamiliar faces/names, the participant may be tested or assessed at the end of the exercise using different faces/names from those used in the exercise, i.e., different from those the participant was trained with.

In some embodiments, the method may also include performing a plurality of practice trials, i.e., prior to performing the method elements described above. For example, in some embodiments, one or more practice sessions may be performed prior to the beginning of training to familiarize the participant with the nature and mechanisms of the exercise, i.e., the learning and testing phases of the exercise. In each practice session, a specified number of trial groups (e.g., 1) for each of one or more practice conditions may be performed. In some embodiments, the participant may be able to invoke such practice sessions at will during the exercise, e.g., to re-familiarize the participant with the task at hand.

Other features and advantages of the present invention will become apparent upon study of the remaining portions of the specification and drawings.

DETAILED DESCRIPTION

Figure 1:
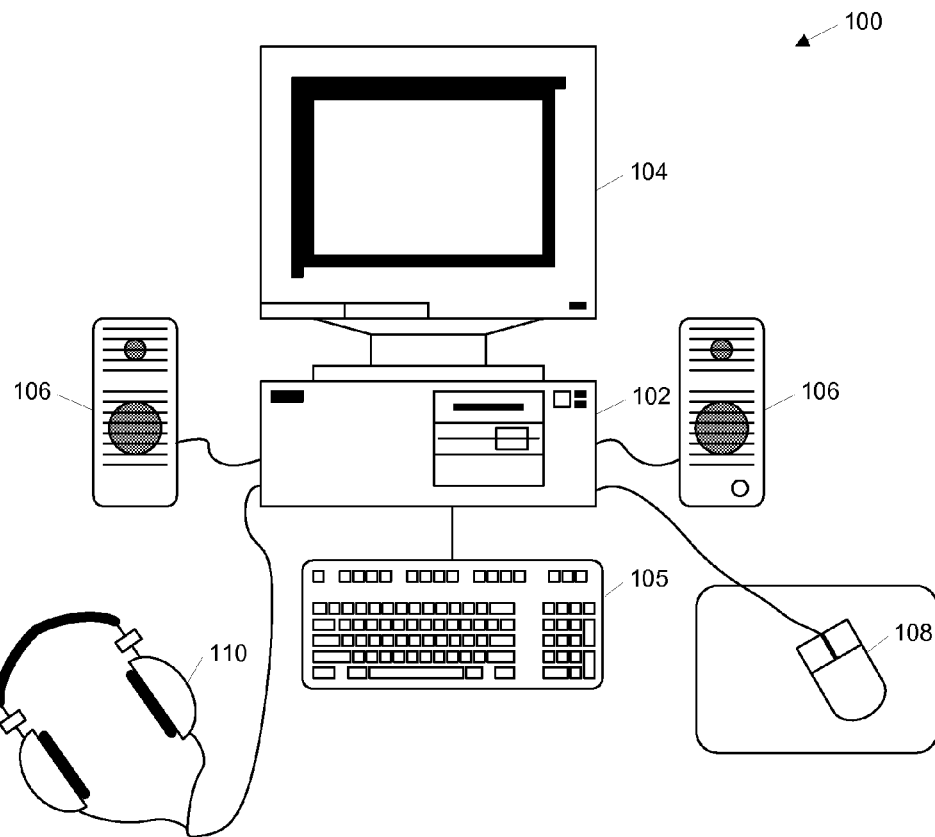
FIG. 1 is a block diagram of a computer system for executing a program according to some embodiments of the present invention.

Referring to FIG. 1, a computer system 100 is shown for executing a computer program to train, or retrain an individual according to the present invention to enhance cognition, where the term "cognition" refers to the speed, accuracy and reliability of processing of information, and attention and/or memory, and where the term "attention" refers to the facilitation of a target and/or suppression of a non-target over a given spatial extent, object-specific area or time window. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. In some embodiments, the speakers 106 and the headphones 110 may provide auditory prompting and feedback to the subject during execution of the computer program. The mouse 108 allows the subject to navigate through the computer program, and to select particular responses after visual or auditory prompting by the computer program. The keyboard 105 allows an instructor to enter alphanumeric information about the subject into the computer 102. Although a number of different computer platforms are applicable to the present invention, embodiments of the present invention execute on either IBM compatible computers or Macintosh computers, or similarly configured computing devices such as set top boxes, PDA's, gaming consoles, etc.

Figure 2:
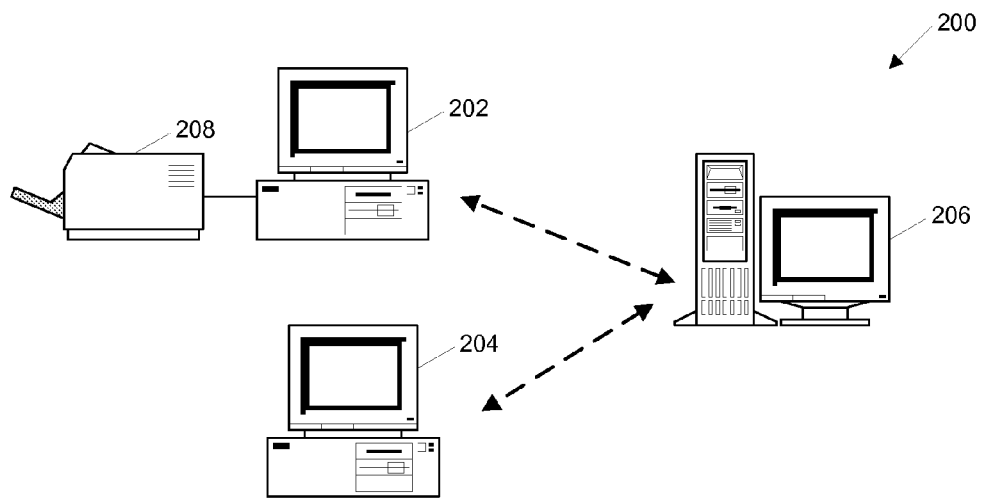
FIG. 2 is a block diagram of a computer network for executing a program according to some embodiments of the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can review the information and can then download configuration and control information pertaining to a particular subject, back to the subject's computer 202, 204.

Overview of the Face-Name Association Exercise

Embodiments of the computer-based exercise described herein may operate to improve a participant's cognition, e.g., renormalizing and improving the ability of the visual nervous system of a participant to associate faces with names.

A primary goal of the exercise described herein is to improve the ability of the brain to accurately associate or bind faces with their appropriate proper name. An additional goal is to exercise the face processing areas of the brain, for example the fusiform face area, the brain system thought to be responsible for making expert-level visual distinctions. The task may engage the participant in encoding a series of face images, along with their designated names, and then associating the unlabeled face with its appropriate identifier (i.e., name). In some embodiments, the face stimuli may be repeatedly flashed on the screen rather than presented statically, as the visual system is strongly engaged by patterns that alternate at intermediate temporal frequency modulations. Thus, flashing the face rather than presenting it at 0 Hz (i.e., a static image) may more strongly engage the neural systems that support learning. Additionally, the onset of visual presentations of the faces may coincide with a synchronous-onset presentation of the spoken proper name. This synchronous presentation may effectively and repeatedly engage the to-be-associated visual and auditory representations, i.e., the face and name.

Making these face-name associations made under conditions of intense synchronous visual and auditory system activation and high levels of attention and reward may drive changes in the mechanisms responsible for recognizing distinguishable human facial characteristics, remembering proper names, and associating these individual units of information into a cohesive unit for identification. The face-name associations formed in this way may be very robust, allowing individuals to easily and reliably recognize and recall the names of individuals around them based on sight, thus greatly facilitating interaction in a wide array of social situations.

In some embodiments, the presentation time of the stimuli, i.e., the length of time the face is shown, referred to as duration, may adapt to track the participant's performance. For example, as the participant improves in ability to associate faces with names, the presentation time or duration may be decreased, thereby making the association task more difficult. Similarly, if the participant does not improve, the presentation time or duration may be increased. Thus, in some embodiments, an adaptive rule or procedure may be used with respect to the stimulus presentation.

A range of conditions may be used in the training, including faces with different views (e.g., profile, front), genders, ages, expressions, and so forth, as will be discussed in more detail below.

Figure 3:
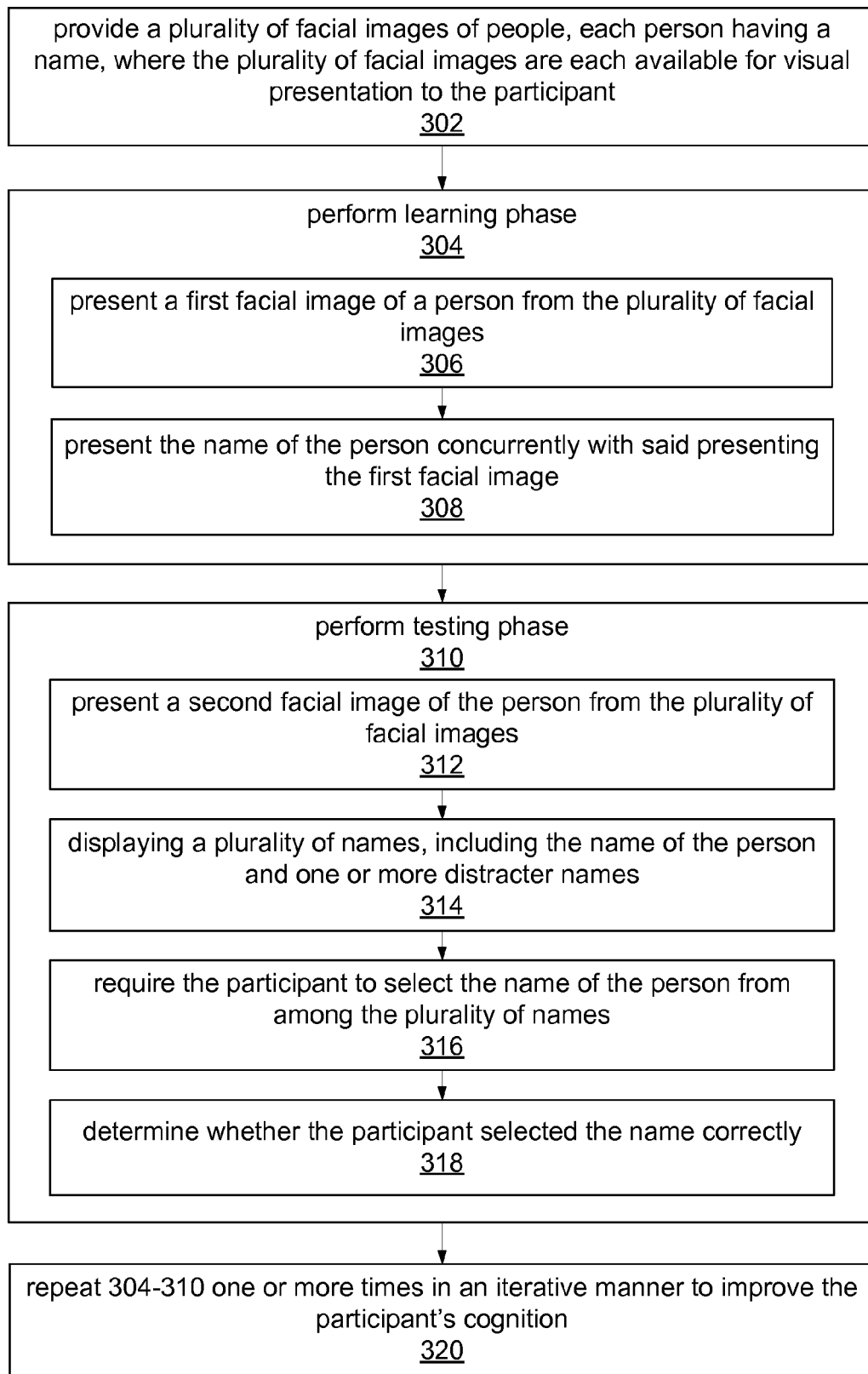
FIG. 3 is a high-level flowchart of one embodiment of a method for cognitive training using face-name associations, according to one embodiment.

FIG. 3—Flowchart of a Method for Cognitive Training Using Face-Name Association

FIG. 3 is a high-level flowchart of one embodiment of a method for cognitive training using face-name association. It should be noted that in various embodiments, some of the method elements may be performed concurrently, in a different order than shown, or may be omitted. Additional method elements may also be performed as desired. In preferred embodiments, the method may be performed in the context of a visual stimulus exercise, e.g., a face-name association exercise, possibly in combination with one or more other visual stimulus exercises. As shown, the method may be performed as follows:

In 302, a plurality of facial images of people may be provided, where each person has a name. The plurality of facial images may each be available for visual presentation to the participant. The plurality of facial images provided may depend on the context in which the exercise is performed. For example, in some embodiments, the exercise may be directed to improving name-face association of a participant with respect to people that are (or should be) familiar to the participant. As one example, the participant may be a resident of a facility, such as a nursing home, where the plurality of facial images may include those of co-residents and/or staff of the nursing home. As another example, the participant may be an employee of a company or institution, and the plurality of facial images may include those of the employees of the company or institution. Of course, these are but two examples of contexts with familiar faces, and any other such contexts are also contemplated, e.g., school, communities, etc. In these (familiar) contexts, in addition to improving cognition, e.g., improving face-name association skills in the participant, the exercise may further serve to familiarize the participant with the people with whom the participant interacts in the facility, company, or institution, thereby providing immediate and direct practical benefits, as well as improving the cognition of the participant.

In other embodiments, the plurality of facial images may not be familiar to the participant. For example, a large number (e.g., 300) of pictures of different faces (e.g., male and female between 18 and 90 years of age) may be used that include various different expressions, facial orientations, etc. In one embodiment, the pictures may be selected from a face database. In these (unfamiliar) contexts, the exercise may improve the cognitive skills of the participant (including, for example, memory skills), as well as improving the participant's particular skills of face-name association, which is of general benefit in social domains.

Note that in both kinds of context (familiar and unfamiliar faces), stimuli, i.e., facial images, with unusual features (e.g., hats) are preferably not used. The images may be standardized with respect to frame, size, luminosity and contrast. In higher stages of the exercise, morphing may be used to create ever-increasing difficulty in making face identifications.

In 304, a learning phase of the method or exercise may be performed, including method elements 306 and 308, described below. In the learning phase, the participant is given a chance to learn a face/name association, and then, in a subsequent testing phase, described below, the participant is tested with respect to this association, and possibly others. In one embodiment, this learning and testing with respect to a face/name pair may compose a trial in the exercise, although in other embodiments, a trial may comprise such learning and testing with respect to all faces and names in a trial group (e.g., five faces/names). The learning phase is now described.

Figure 4:
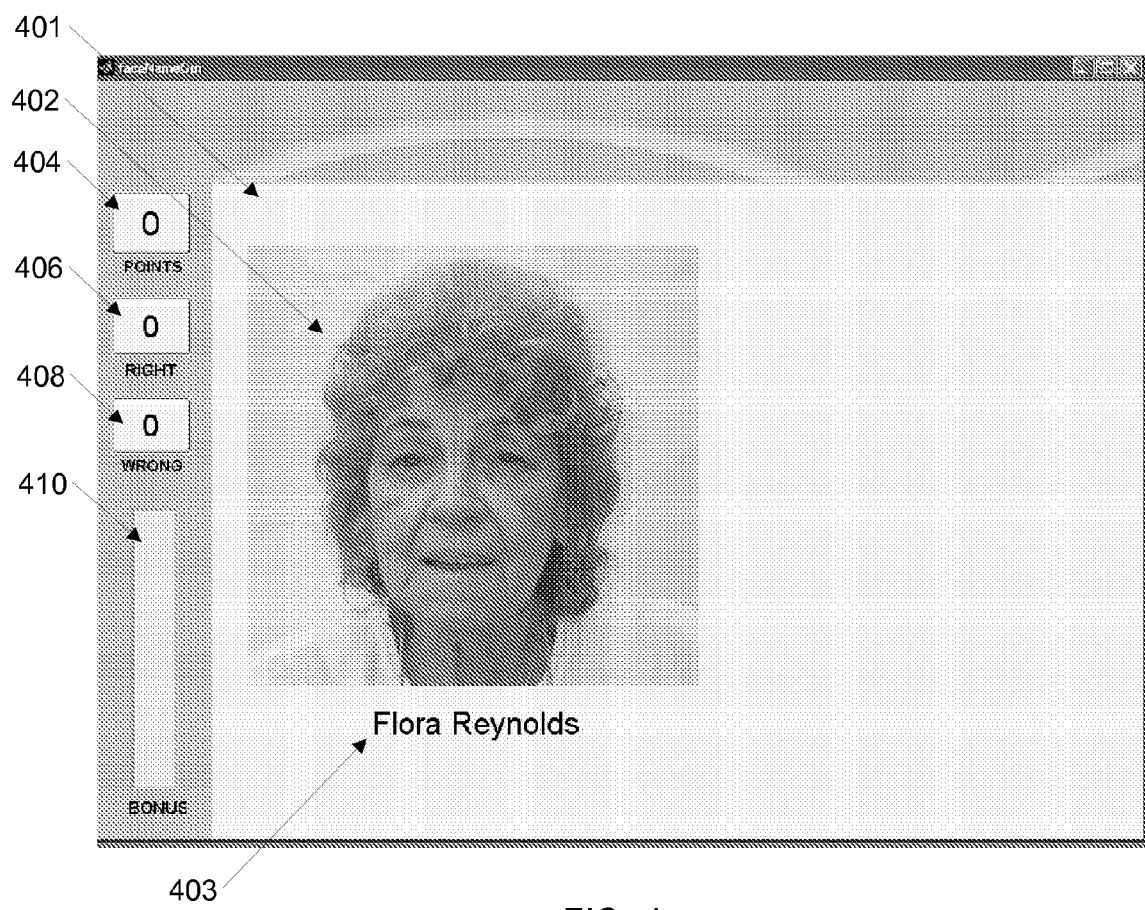
FIG. 4 illustrates an exemplary screenshot of a graphical user interface (GUI) for the learning phase of the face-name association exercise, according to one embodiment.

In 306, a first facial image of a person from the plurality of facial images may be presented. For example, the first facial image may be displayed in a display area of a graphical user interface (GUI), as illustrated in FIG. 4 and described below.

In 308, the name of the person may be presented concurrently with the presenting of the first facial image (of 306). In other words, a first facial image of a person and the name of the person may be presented to the participant at the same time. Note that the name may be presented graphically and/or audibly (verbally). In other words, presenting the name may include textually presenting the name and/or auditorily presenting the name. Moreover, auditorily presenting the name may include a synchronous-onset presentation of the name with said presenting the facial image. In other words, the name may be played when the facial image is first displayed.

In some embodiments, presenting the first facial image may include flashing the facial image at a specified rate, e.g., between 1 and 4 Hz, although any other rate may be used as desired. Similarly, presenting the name of the person may include repeating the name at a specified rate (graphically and/or audibly), preferably the same rate at which the facial image is flashed. In one embodiment, the name may be presented graphically and verbally, where the graphical name is static, and the verbal presentation of the name is repeated with the facial image.

The human visual system is strongly engaged by patterns that alternate at intermediate temporal frequency modulations. Thus, flashing the face rather than presenting it at 0 Hz (i.e., as a static image) may more strongly engage the neural systems that support learning. Additionally, the onset of visual presentation of the face may be associated with a synchronous-onset presentation of the (displayed and/or spoken) proper name, which may effectively and repeatedly engage the to-be-associated visual and auditory representations.

In preferred embodiments, the participant may perform the exercise described herein via a graphical user interface (GUI). FIG. 4 illustrates an exemplary screenshot of a graphical user interface (GUI) for the face-name association exercise, according to one embodiment, specifically, for the learning phase of the face-name association exercise. As may be seen, the GUI preferably includes a visual field 401, in which may be displayed a facial image of a person 402, e.g., the first facial image of 306. As also shown, in this embodiment, the name of the person 403 is also displayed, e.g., the name of the person of 308. As noted above, in some embodiments, the name may also (or instead) be verbally or audibly presented. As also noted above, the face and verbal name may be repeated at a specified rate, e.g., for a specified time.

As FIG. 4 also shows, in this embodiment, the GUI may include one or more of: a score indicator 404, an indicator of how many correct associations the participant has made 406, and indicator of how many incorrect association the participant has made 408, and a bonus meter 410 that indicates how close the participant is to getting bonus points in each trial group. Of course, the GUI of FIG. 4 is meant to be exemplary only, and is not intended to limit the GUI to any particular form, functionality, or appearance.

In various embodiments, and over the course of the exercise, the presenting of 304 may be performed under a variety of specified conditions that may make performing the task more or less difficult. For example, the presentation time for the facial image and the name may be shortened to increase the difficulty of the task, or lengthened to make the task easier. Other conditions may also be used, such as, for example, the orientation or expression of the facial images, as will be described below in detail.

In 310, a testing phase of the exercise may be performed, including method elements 312, 314, 316, and 318, described below. As indicated above, in the testing phase, the participant is tested with respect to the face/name presented in the learning phase, and may also be tested on previously presented face/name pairs, as will be discussed below. The testing phase is now described.

In 312, a second facial image of the person from the plurality of facial images may be presented. In some embodiments, the second facial image is the same image as the first facial image. However, in other embodiments, the second facial image and the first facial image may differ. For example, the first and second facial images of the person may differ in view and/or expression, where the view of a facial image refers to the orientation of the face, e.g., front view, profile, and so forth. In some embodiments, one or more of the first and second facial images may be morphed, i.e., stretched, compressed, or otherwise distorted, to increase the difficulty of the task.

In 314, a plurality of names, including the name of the person and one or more distracter names, may be presented.

In other words, a list of names may be presented, e.g., next to the second facial image, that includes the name of the person (of the first and second facial images) and one or more other names. These distracter names may include names of previously presented facial images and/or names not associated with any facial images. In preferred embodiments, the number of names presented may vary from trial to trial, as will be discuss below in more detail.

Figure 5:
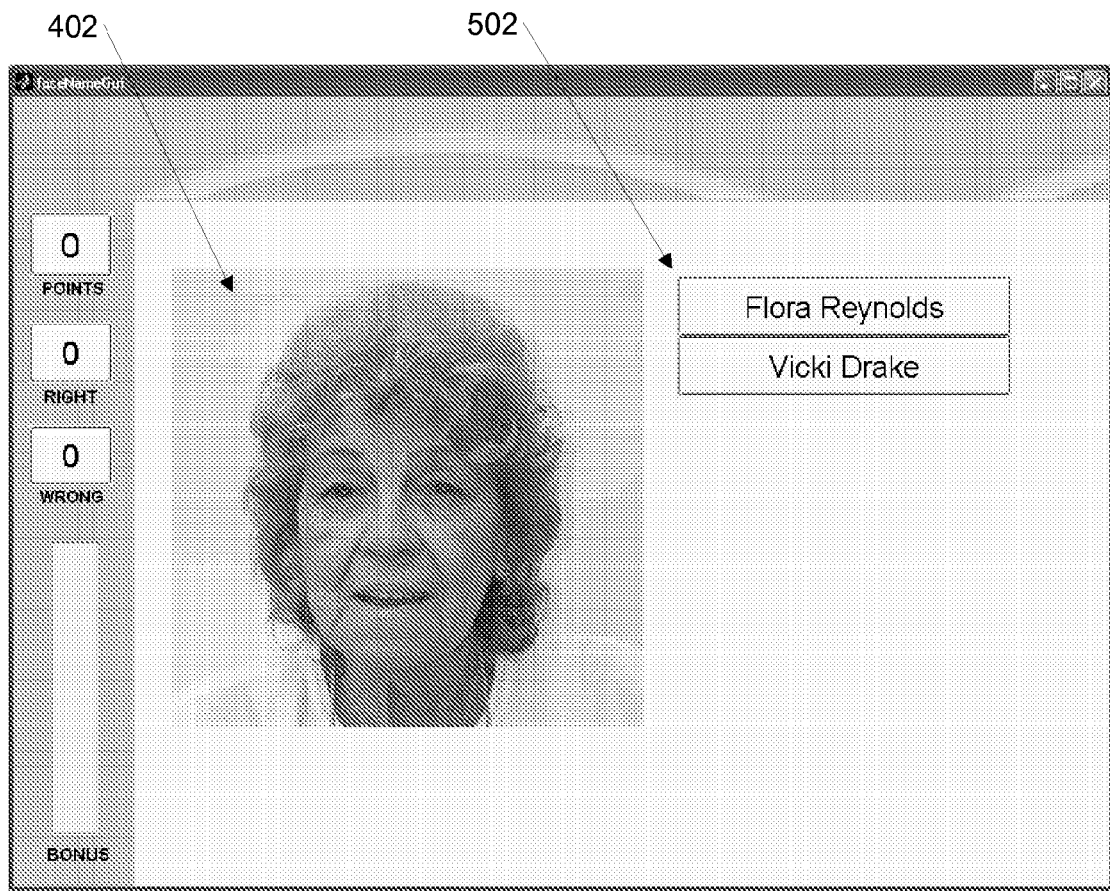
FIG. 5 illustrates an exemplary screenshot of a GUI for the testing phase of the face-name association exercise, according to one embodiment.

FIG. 5 illustrates an exemplary screenshot of a GUI for the testing phase of the face-name association exercise. As shown, in this embodiment, the second facial image 402 is the same as that presented in the learning phase, illustrates in FIG. 4. As also shown, FIG. 5 displays a list of selectable names 502, including the name of the person, in this case, Flora Reynolds, and one distracter name—Vicki Drake.

In 316, the participant may be required to select the name of the person from the plurality of names. For example, input from the participant selecting the name may be received, and the selection made by the participant may be recorded. In one embodiment, the name may be selected by the participant placing a cursor over the name to be selected and clicking a mouse, although other selection means may be used as desired, e.g., using arrow keys to navigate through the list, and pressing the enter key, using a menu, etc.

In 318, a determination may be made as to whether the participant selected the name correctly. The correctness or incorrectness of the selection is preferably recorded. In other words, the participant's success at selecting the name may be recorded.

In some embodiments, an indication of the correctness or incorrectness of the selection may be provided, e.g., graphically and/or audibly. For example, in some embodiments, a sound, such as a "ding" or "thunk", may be played to indicate the correctness or incorrectness, respectively, of the selection. It should be noted, however, that any other kind of indication may be used as desired, e.g., a reward animation, etc.

In one embodiment, points may be awarded based on the correctness of the selection, which may be reflected by the score indicator 404 of the GUI. Similarly, in some embodiments, based on the correctness/incorrectness of the selection, the indicator of how many correct associations the participant has made 406 or the indicator of how many incorrect associations the participant has made 408 may be updated accordingly.

In one exemplary reward scheme, the participants may receive immediate auditory feedback depending on if the right or wrong associations is made, and rewarded points depending on the right or wrong associations, e.g., every right association may be rewarded with 10 points. The number of right and wrong associations may always be displayed (via indicators 406 and 408). Bonus points may be awarded for every five consecutive correct associations made in the first trial group, and for every seven right associations made in consecutive trial groups. The bonus meter 410 may indicate how close the participant is to getting bonus points in each trial group.

Finally, as indicated in 320, the above learning phase and testing phase may be performed one or more times in an iterative manner to improve the participant's cognition, e.g., face-name association skills.

In other words, a plurality of trials may be performed in the exercise as described above. For example, the repetitions may be performed over a plurality of sessions, e.g., over days, weeks, or even months, e.g., for a specified number of times per day, and for a specified number of days. In some embodiments, at the end of each session, the participant's score for the session may be shown and may be compared to the best prior performance for that participant.

Such repeating preferably includes performing a plurality of trials under each of a plurality of conditions, where each condition specifies one or more attributes of the plurality of images or their presentation. Thus, groups of stimuli, referred to as trial groups, may contain or embody particular conditions affecting the difficulty of the face-name association task. A typical trial group may include 5 faces/names, although other numbers may be used as desired. Thus, the plurality of facial images may include a plurality of groups of facial images, where the repeating may include: for each group, performing the learning phase and the testing phase for each facial image in the group.

For example, the plurality of facial images may include one or more stimulus categories, each stimulus category specifying a relationship between the first and second facial images in the stimulus category. In some embodiments, the one or more stimulus categories include one or more of: a single view category, where the first and second facial images have the same view, a multiple view category, where the first and second facial images have different views, and a multiple expression category, where the first and second facial images have different expressions. Thus, even though each facial image pair (i.e., the first and second facial images of the learning and testing phases) illustrates the same person, the images may (or may not) differ from each other. Thus, the repeating may include progressing through groups of facial images in each of the one or more stimulus categories.

In some embodiments, each category may have a respective plurality of subcategories further specifying the relationship between first and second facial images in the category. For example, the subcategories may include two or more of: an age and gender independent subcategory, where the person of the first and second facial images is unconstrained with respect to age and gender, a gender specific subcategory, where the person of the first and second facial images is constrained with respect to gender, and an age specific subcategory, where the person of the first and second facial images is constrained with respect to age. In these embodiments, progressing through groups of facial images in each of the one or more stimulus categories may include: for each stimulus category, progressing through groups of facial images in each subcategory of the stimulus category.

The following summarizes an exemplary matrix of conditions suitable for use in some embodiments of the exercise:

|  | Single view (Front view Vs Front view) | Multiple views (Front view Vs Profile view) | Multiple expressions. (Neutral expression Vs Happy expression) |
| --- | --- | --- | --- |
| Age and gender independent | Category 1a | Category2a | Category3a |
| Gender specific | Category1b | Category2b | Category3b |
| Age and gender specific | Category1c | Category2c | Category3c |

The participant may progress through a plurality of trial groups of the exercise based on the participant's success rate at each trial group, where each trial group may be associated with respective subsets of the conditions (e.g., one condition per trial group). Thus, for example, initial trial groups may include trials performed under the easiest conditions, and successive, more difficult, trial groups may include trials performed under more difficult conditions. An example of an easier trial group is one in which the names/faces in the group are all of the same gender, and in which the first and second facial images (of the learning phase and the testing phase, respectively) are the same. An example of a more difficult trial group is one in which the trial group includes faces/names of both genders, and where the first and second facial images differ in orientation (e.g., front view vs. profile) and facial expression (solemn vs. smiling). The trial groups may continue until the participant has mastered all the faces and names in all categories.

In some embodiments, the conditions of the stimuli (i.e., faces/names) used may depend upon the context of the exercise. For example, in some embodiments using familiar faces/names, the facial images may have various orientations and expressions (expressing various emotions, e.g., neutral/happy/sad/annoyed, etc.), mixed genders within a trial group, and so forth, whereas in some embodiments using unfamiliar faces/names, the facial images may all have the same orientation (e.g., front view) and expression (e.g., neutral), gender specific trial groups, etc. However, it should be noted that any conditions may be used as desired in both the familiar and unfamiliar contexts.

In some embodiments, the progression through each trial group may be progressive, where, for each face/name pair from the trial group presented to the participant, the participant is tested on that face/name pair, plus all face/name pairs previously presented from the trial group. Moreover, in some embodiments, one or more, e.g., two, additional face/name pairs from a previous trial group may also be included in the testing. The following describes an exemplary embodiment of such a progression.

In some embodiments, performing the testing phase for each facial image in the group may include: for each facial image in the group, referred to as the first group, and for each facial image in a second group including the facial image (or another facial image of the same person), previously presented facial images from the first group, and zero or more previously presented facial images from a previous group, a) presenting a randomly selected facial image of a person from the second group, b) displaying a second plurality of names, including the name for each facial image in the second group, and one or more distracter names, c) requiring the participant to select the name of the person for the randomly selected facial image from the plurality of names; and d) determining whether the participant correctly selected the name of the person for the randomly selected facial image.

In other words, after each face/name from the trial group, i.e., the first group, is presented in the learning phase, the participant is tested on all the faces/names in a second group, comprising the most recent face/name, all previously presented faces/names from the first (trial) group, plus one or more distracter names, plus zero or more faces/names from the previous trial group. Thus, each time a new face/name from the trial group is presented in the learning phase, the list of selectable names presented in the testing phase may increase by one. Said another way, as the participant progresses through the trial group, the number of names/faces tested on increases, as all previous faces/names are included in the testing. In various embodiments, the number of additional faces/names from the previous trial group used in the testing phase may be zero, one, two, or any other number, as desired. It should be noted that in various embodiments, the distracter name may be constant for a trial group, or may change, e.g., in response to the participant's selection(s), or even per selection task.

Moreover, in some embodiments, the repeating may further include: if the participant incorrectly selected the name of the person for the randomly selected facial image, performing the learning phase again for the randomly selected facial image, and performing a)-d) for each facial image in the second group. In other words, each time the participant selects a wrong name, the learning phase for the current face/name may be performed, then the above progressive learning phase. This repetition may serve to reinforce previously "learned" face/name pairs, and to accelerate the improvement of the participant's face/name association skills. Note also that as the participant makes correct associations, the task gets progressively harder as the participant has to remember all face-name pairs learned to that point (for that trial group).

As noted above, participants may move through all subcategories within a category before moving to the next category. Within each subcategory, participants move through trial groups or stages (i.e., with increasing numbers of response buttons) and then advance through categories or levels (age and gender specific) based on performance. Note that progression in the exercise is designed to allow participants with poor face-name association ability to advance through tasks without getting stuck by retraining them on the face-name pairs for which wrong associations are made.

Note that in some embodiments, the initial trial group may be handled differently from subsequent trial groups (see, e.g., FIG. 5). For example, no additional faces/names from previous trial groups may be included, since there are no previous trials groups initially. Thus, for example, with respect to the initial trial group (of FIG. 5), the possible selections for the first face/name association are limited to two names—the name of the person whose face is displayed, and one distracter name. In contrast, with respect to a subsequent (non-initial) trial group, at the start of the learning phase of the trial group the user is trained on a new face. However, during the test phase, unlike the first trial group, the user is tested on the new face and two randomly chosen faces from the previous trial group. As a result, beginning from the second trial group, all consecutive trials may end with being tested on seven face-name pairs (plus one distracter name), as discussed below with reference to FIG. 8.

Additionally, as indicated above, in some embodiments, for the first trial group, bonus points may be awarded for five consecutive correct associations (since only five faces/names are learned and tested on), whereas in subsequent trial groups, seven consecutive correct associations may be required for bonus points (since the participant is tested on the five faces/names of the current trial group, plus two previously learned faces/names).

Figure 6:
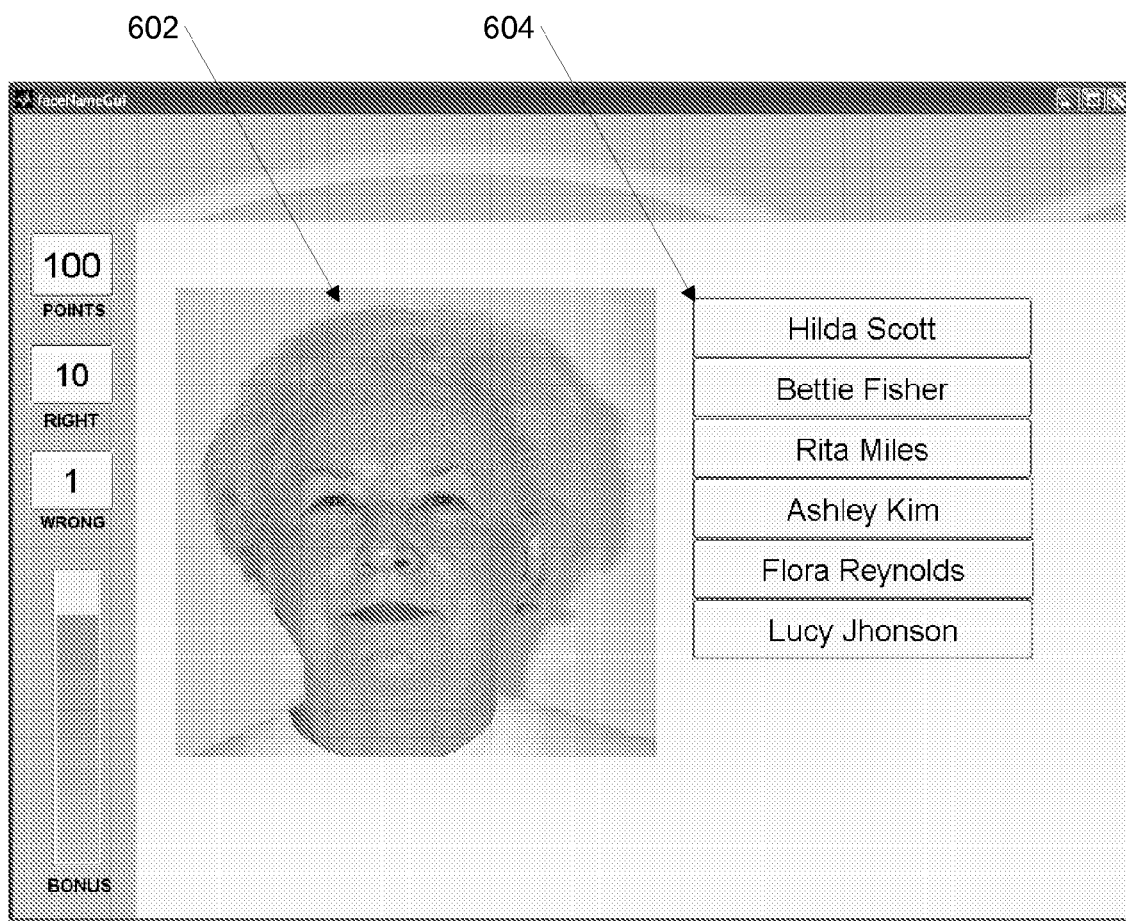
FIG. 6 illustrates another exemplary screenshot of a GUI for the testing phase of the face-name association exercise, according to one embodiment.

FIG. 6 illustrates an exemplary screenshot of the GUI where six names 604 are displayed for selection (for possible association with displayed facial image 602), and so may correspond to the final portion of the initial trial group introduced with reference to FIG. 5, described above, where the listed names are those of the initial trial group plus one distracter name. Note that the bonus meter indicates that the participant has responded correctly four times consecutively, and thus is one correct response away from receiving bonus points (assuming this is the initial trial group).

Figure 7:
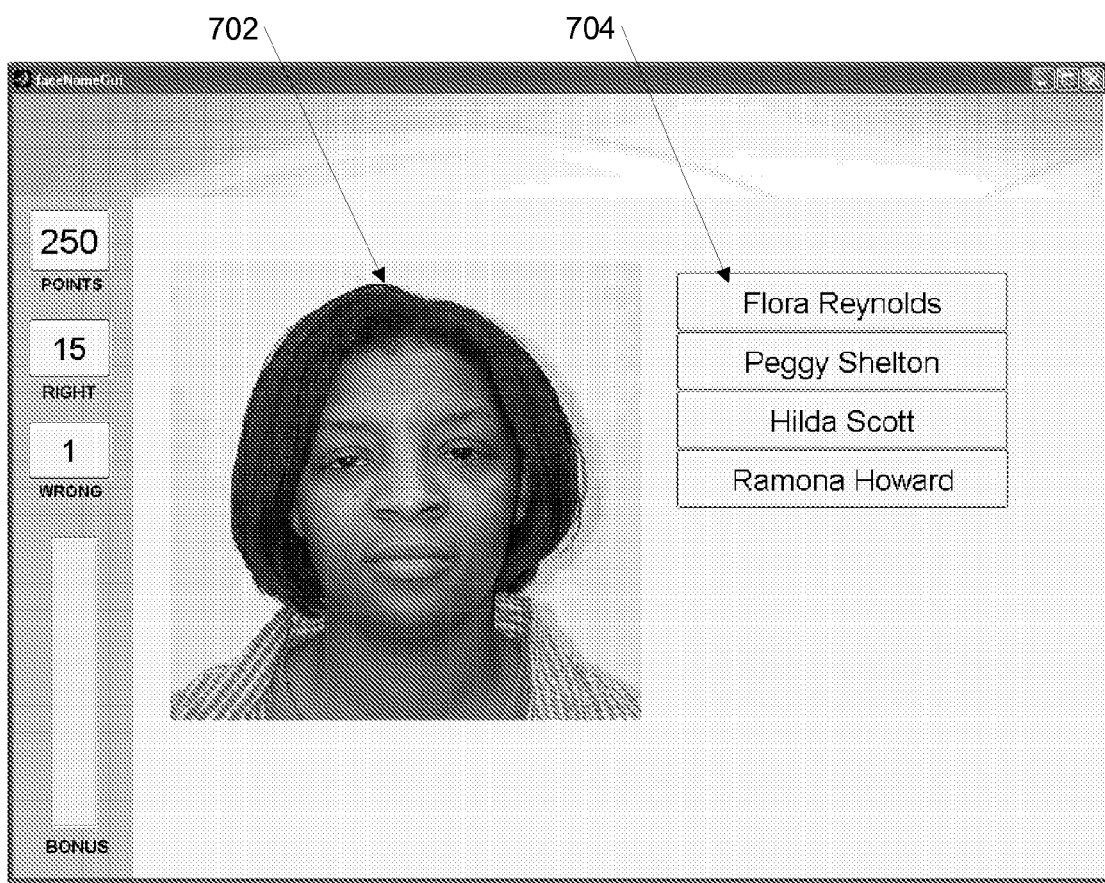
FIG. 7 illustrates a further exemplary screenshot of a GUI for the testing phase of the face-name association exercise, according to one embodiment.
Figure 8:
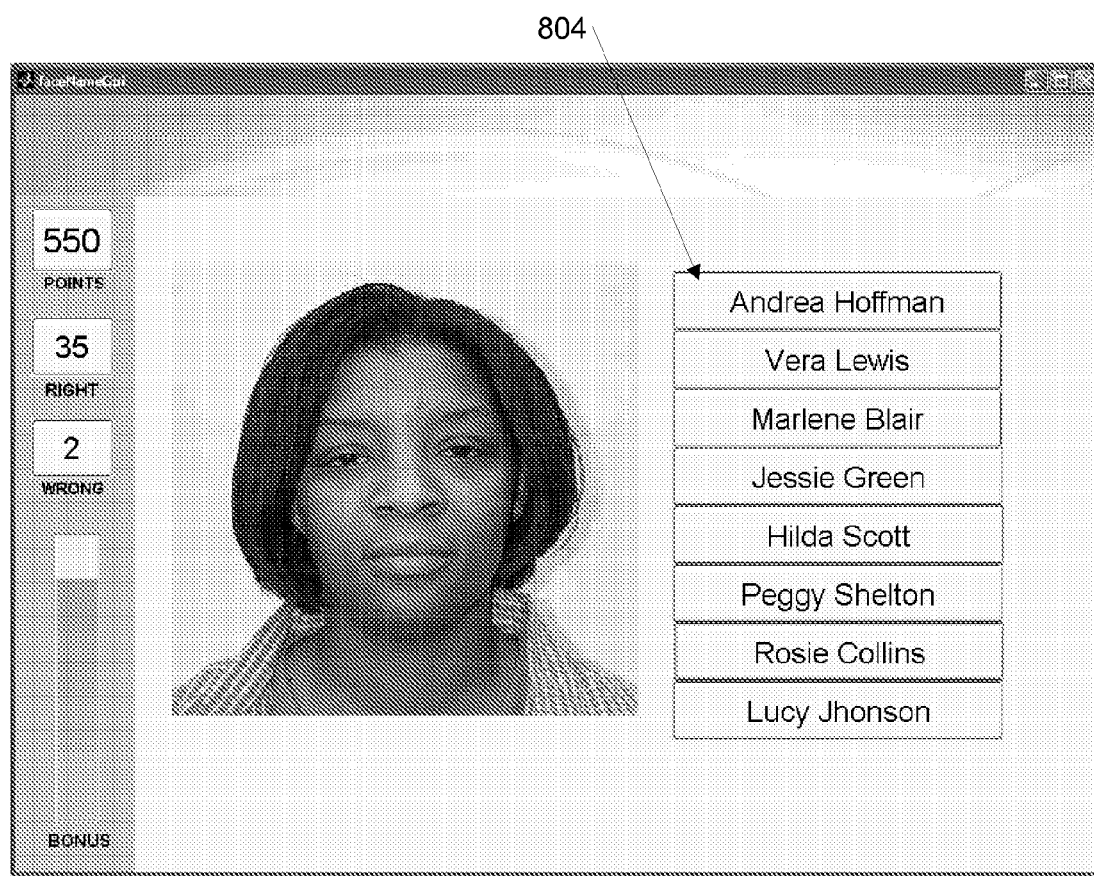
FIG. 8 illustrates another exemplary screenshot of a GUI for the testing phase of the face-name association exercise, according to one embodiment.

In contrast, FIGS. 7 and 8 illustrate exemplary screenshots of the GUI corresponding to a subsequent trial group, where the participant must select from progressively larger lists of names. As may be seen, FIG. 7 illustrates an exemplary screenshot of the GUI where four names 704 are displayed for selection (for possible association with displayed facial image 702), and so corresponds to an intermediary point of a subsequent or non-initial trial group, where the listed names include three selected (e.g., randomly) from the group comprising the trial group and two names from a previous trial group, plus a distracter name.

FIG. 8 illustrates an exemplary screenshot of the GUI where eight names 804 are displayed for selection, and so may correspond to the latter portion of the trial group of FIG. 7, where the listed names are those of the (non-initial) trial group, plus two names from a previous trial group, plus a distracter name. As may be seen, the particular selection tasks corresponding to FIGS. 7 and 8 are progressively more difficult, due to the increasing numbers of names from which to select.

In some embodiments, one or more assessments of the participant's face/name association skills may be made, e.g., before, during, and/or after the exercise. The stimuli (i.e., faces/names) used in the assessment may depend upon the context of the exercise. For example, in embodiments using familiar faces/names, the participant's knowledge (i.e., ability to associate) of all faces may be tested at the beginning and end of the exercise. In embodiments using unfamiliar faces/names, the participant may be tested or assessed at the end of the exercise using different faces/names from those used in the exercise, i.e., different from those the participant was trained with.

In some embodiments, certain information may be maintained and recorded over the course of the exercise. For example, in one exemplary embodiment, the following information may be recorded: the name of the participant; the age of the participant; the gender of the participant; the number of trial groups completed; all scores achieved during the exercise; the conditions in force for each trial group; time/date for each session; and time spent on each trial group, among others. Of course, this information is meant to be exemplary only, and other information may be recorded as desired.

In some embodiments, the method may also include performing a plurality of practice trials, i.e., prior to performing the method elements described above. For example, in some embodiments, one or more practice sessions may be performed prior to the beginning of training to familiarize the participant with the nature and mechanisms of the exercise, i.e., the learning and testing phases of the exercise. In each practice session, a specified number of trial groups (e.g., 1) for each of one or more practice conditions may be performed. In some embodiments, the participant may be able to invoke such practice sessions at will during the exercise, e.g., to re-familiarize the participant with the task at hand.

It should be noted that the particular exercise disclosed herein is meant to be exemplary, and that other repetition-based cognitive training exercises using visual stimuli with multiple stimulus sets may be used as desired, possibly in combination. In other words, the face-name association exercise described herein is but one example of a cognitive training exercise using a computing system to present visual stimuli to a participant, record the participant's responses, and modify some aspect of the visual stimuli based on these responses, where these method elements are repeated in an iterative manner using multiple sets of stimuli to improve cognition, e.g., the ability of the participant to process visual information. Note particularly that such cognitive training using a variety of such visual stimulus-based exercises, possibly in a coordinated manner, is contemplated.

Those skilled in the art should appreciate that they can readily use the disclosed conception and specific embodiments as a basis for designing or modifying other structures for carrying out the same purposes of the present invention without departing from the spirit and scope of the invention as defined by the appended claims. For example, various embodiments of the methods disclosed herein may be implemented by program instructions stored on a memory medium, or a plurality of memory media.

We claim:

1. A method for enhancing cognition in a participant, utilizing a computing device to present visual stimuli for training, and to record responses from the participant, the method comprising:
   providing a plurality of facial images of people, each person having a name, wherein the plurality of facial images are each available for visual presentation to the participant;
   performing a learning phase, comprising:
      presenting a first facial image of a person from the plurality of facial images; and
      presenting the name of the person concurrently with said presenting the first facial image;
   performing a testing phase, comprising:
      presenting a second facial image of the person, distinct from the first facial image in that the second facial image is a morphed image of the person, from the plurality of facial images;
      displaying a plurality of names, including the name of the person and one or more distracter names;
      requiring the participant to select the name of the person from the plurality of names; and
      the computing device determining whether the participant selected the name correctly; and
   repeating said performing the learning phase and said performing the testing phase one or more times in an iterative manner to improve the participant's cognition;
   wherein the use of a morphed second facial image, wherein the form and/or shape of the facial image is distorted, increases the difficulty of selecting the name of the facial image.

2. The method of claim 1, wherein the plurality of facial images comprises a plurality of groups of facial images, wherein said repeating comprises:
   for each group, performing the learning phase and performing the testing phase for each facial image in the group.

3. The method of claim 2, wherein the plurality of facial images of people comprises facial images of people that are familiar to the participant.

4. The method of claim 3, further comprising:
   assessing the participant's face-name associations before and/or after said repeating, using the facial images of people that are familiar to the participant.

5. The method of claim 2, wherein the plurality of facial images of people comprises facial images of people that are unfamiliar to the participant.

6. The method of claim 5, further comprising:
   assessing the participant's face-name associations before and/or after said repeating, using facial images of people that are unfamiliar to the participant, and that are not included in the plurality of facial images.

7. The method of claim 1, further comprising:
   a) randomly selecting facial images for presentation during the testing phase, wherein the facial images are randomly selected from a group comprising the most recent facial image presented during the most recent trial phase and previously presented facial images;
   b) displaying a second plurality of names, including the name for each facial image in the group, and one or more distracter names;

c) requiring the participant to select the name of the person for the randomly selected facial image from the second plurality of names; and d) determining whether the participant correctly selected the name of the person for the randomly selected facial image.

8. The method of claim 7, wherein the group consists of the most recent facial image presented during the most recent trial phase and previously presented facial images.

9. The method of claim 7, wherein said repeating further comprises:
if the participant incorrectly selected the name of the person for the randomly selected facial image,
performing the learning phase again for the randomly selected facial image; and
performing a)-d) for each facial image in the group.

10. The method of claim 1, wherein said requiring the participant to select the name comprises:
receiving input from the participant selecting the name; and
recording the selection made by the participant.

11. The method of claim 1, wherein said presenting the name comprises both:
textually presenting the name; and
auditorily presenting the name.

12. The method of claim 11, wherein said auditorily presenting the name comprises:
a synchronous-onset presentation of the name with said presenting the facial image.

13. The method of claim 1, wherein said presenting the name of the person during the learning phase comprises:
repeating the name multiple times in rapid succession.

14. The method of claim 1, further comprising:
recording the participant's success at selecting the name.

15. The method of claim 1, further comprising:
indicating whether the participant selected the name correctly, wherein said indicating is performed audibly and/or graphically.

16. The method of claim 1, further comprising:
awarding points based on the correctness of the participant's selection.

17. The method of claim 1, further comprising:
awarding bonus points if the participant selects the name correctly a specified number of times consecutively.

18. The method of claim 1, further comprising:
performing trials in one or more practice sessions to familiarize the participant with the learning phase and the testing phase.

19. The method of claim 1, wherein said repeating occurs a specified number of times each day, for a specified number of days.

20. A method for enhancing cognition in a participant, utilizing a computing device to present visual stimuli for training, and to record responses from the participant, the method comprising:
providing a plurality of facial images of people, each person having a name, wherein the plurality of facial images are each available for visual presentation to the participant;
performing a learning phase, comprising:
presenting a first facial image of a person from the plurality of facial images by repeatedly and visibly flashing the first facial image multiple times in rapid succession; and
presenting the name of the person concurrently with said presenting the first facial image;
performing a testing phase, comprising:
presenting a second facial image of the person, distinct from the first facial image in that the second facial image comprises a different view or expression of the person, from the plurality of facial images;
displaying a plurality of names, including the name of the person and one or more distracter names;
requiring the participant to select the name of the person from the plurality of names; and
the computing device determining whether the participant selected the name correctly; and
repeating said performing the learning phase and said performing the testing phase one or more times in an iterative manner to improve the participant's cognition.

21. The method of claim 20, wherein the second facial image and the first facial image depict different emotional-connotive facial expressions of the same person.

22. The method of claim 20, wherein the plurality of facial images comprises one or more stimulus categories, each stimulus category specifying a relationship between the first and second facial images in the stimulus category.

23. The method of claim 22, where the one or more stimulus categories comprise one or more of:
a single view category, wherein the first and second facial images have the same view;
a multiple view category, wherein the first and second facial images have different views; and
a multiple expression category, wherein the first and second facial images have different expressions.

24. The method of claim 23, wherein said repeating comprises progressing through groups of facial images in each of the one or more stimulus categories.

25. The method of claim 22, wherein each category has a respective plurality of subcategories further specifying the relationship between first and second facial images in the category.

26. The method of claim 25, where the subcategories comprise two or more of:
an age and gender independent subcategory, wherein the person of the first and second facial images is unconstrained with respect to age and gender;
a gender specific subcategory, wherein the person of the first and second facial images is constrained with respect to gender; and
an age specific subcategory, wherein the person of the first and second facial images is constrained with respect to age.

27. The method of claim 25, wherein said repeating comprises progressing through groups of facial images in each of the one or more stimulus categories, comprising:
for each stimulus category, progressing through groups of facial images in each subcategory of the stimulus category.

28. The method of claim 20, wherein each of the plurality of facial images is standardized with respect to each of:
aspect ratio;
frame;
size;
luminosity; and
contrast.

29. The method of claim 20, wherein the first facial image is flashed at a specified rate of between 1 and 4 Hz.

30. The method of claim 20, wherein the performing a learning phase further comprises:
repeatedly audibly presenting the name of the person concurrently with said flashing of the first facial image.

31. A method for enhancing cognition in a participant, utilizing a computing device to present visual stimuli for training, and to record responses from the participant, the method comprising:
- providing a plurality of facial images of people, each person having a name, wherein the plurality of facial images are each available for visual presentation to the participant;
- performing a learning phase, comprising:
  - presenting a first facial image of a person from the plurality of facial images; and
  - presenting the name of the person concurrently with said presenting the first facial image;
- performing a testing phase, comprising:
  - presenting a second facial image of the person, distinct from the first facial image in that the second facial image comprises a different view or expression of the person, from the plurality of facial images;
  - displaying a plurality of names, including the name of the person and one or more distracter names;
  - requiring the participant to select the name of the person from the plurality of names; and
  - the computing device determining whether the participant selected the name correctly; and
- repeating said performing the learning phase and said performing the testing phase one or more times in an iterative manner to improve the participant's cognition,
- wherein the second facial image is distorted in form or shape in order to increase the difficulty of the testing.

* * * * *